United States Patent [19]
Daute et al.

[11] Patent Number: 5,221,433
[45] Date of Patent: Jun. 22, 1993

[54] DEINKING WASTEPAPER USING ALKOXYLATION PRODUCT OF CARBOXYLIC ACID CONTAINING AN OH GROUP AND ALKYLENE OXIDE

[75] Inventors: Peter Daute, Essen; Gerhard Stoll, Korschenbroich; Klaus Hornfeck, Mettmann, all of Fed. Rep. of Germany

[73] Assignee: Henkel Kommanditgesellschaft auf Aktien, Duesseldorf-Holthausen, Fed. Rep. of Germany

[21] Appl. No.: 807,860

[22] PCT Filed: Jul. 10, 1990

[86] PCT No.: PCT/EP90/01122
§ 371 Date: Jan. 13, 1992
§ 102(e) Date: Jan. 13, 1992

[87] PCT Pub. No.: WO91/01405
PCT Pub. Date: Feb. 7, 1991

[30] Foreign Application Priority Data
Jul. 14, 1989 [DE] Fed. Rep. of Germany ..... 39233393

[51] Int. Cl.⁵ .............................................. D21C 5/02
[52] U.S. Cl. ............................................. 162/5; 162/6; 162/8
[58] Field of Search .............................. 162/4, 5, 6, 7, 8

[56] References Cited

U.S. PATENT DOCUMENTS

| | | | |
|---|---|---|---|
| 4,586,982 | 5/1986 | Pappel et al. | 162/5 |
| 4,964,949 | 10/1990 | Hamaguchi et al. | 162/5 |

FOREIGN PATENT DOCUMENTS

| | | | |
|---|---|---|---|
| 1517172 | 12/1969 | Fed. Rep. of Germany . | |
| 1089394 | 5/1986 | Japan | 162/5 |
| 3050592 | 3/1988 | Japan | 162/5 |
| 1347971 | 2/1974 | United Kingdom . | |

*Primary Examiner*—Karen M. Hastings
*Attorney, Agent, or Firm*—Ernest G. Szoke; Wayne C. Jaeschke; Henry E. Millson, Jr.

[57] ABSTRACT

According to the invention, wastepaper is refined in the presence of alkoxylation products obtainable by reaction of alkylene oxides with $C_{10-22}$ carboxylic acid derivatives and/or $C_{10-22}$ carboxylic acids containing carboxylic acid residues with at least one OH group in the 9, 10, 13 and/or 14 position and the detached printing ink particles are subsequently removed from the paper stock suspensions by flotation or washing.

13 Claims, No Drawings

DEINKING WASTEPAPER USING ALKOXYLATION PRODUCT OF CARBOXYLIC ACID CONTAINING AN OH GROUP AND ALKYLENE OXIDE

This invention relates to a process for regenerating wastepaper and to the use of alkoxylation products of certain $C_{10-22}$ carboxylic acid derivatives containing OH groups and/or certain $C_{10-22}$ carboxylic acids containing OH groups for the regeneration of wastepaper.

Today, wastepaper is used in large quantities for the production of, for example, newsprint and hygiene paper. Lightness and color are important quality features for papers of this type. To achieve this, the printing inks have to be removed from the printed wastepaper. This is normally done by deinking processes essentially comprising two steps, namely:

1. refining the wastepaper, i.e. fiberizing in water in the presence of the chemicals required for detachment of the printing ink particles and
2. removal of the detached printing ink particles from the fiber suspension.

The second step can be carried out by washing or flotation (Ullmanns Encyclopädie der technischen Chemie, 4th Edition, Vol. 17, pages 570-571 (1979)). In flotation, which utilizes the difference in wetability between printing inks and paper fibers, air is forced or drawn through the fiber suspension. Small air bubbles attach themselves to the printing ink particles and form a froth at the surface of the water which is removed by savers.

The deinking of wastepaper is normally carried out at alkaline pH values in the presence of alkali hydroxides, alkali silicates, oxidative bleaches and surfactants at temperatures in the range from 30° to 50° C. Anionic and/or nonionic surfactants, for example soaps, ethoxylated fatty alcohols and/or ethoxylated alkyl phenols are mainly used as surfactants (Wochenblatt für Papierfabrikation 17, 646 to 649 (1985)).

DE-OS 31 01 444 relates to a process for the deinking of wastepaper using a compound corresponding to the following general formula

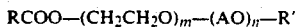

in which is a $C_{7-21}$ alkyl or alkenyl group, R' is a hydrogen atom or a $C_{1-18}$ alkyl, alkenyl or acyl group, AO represents $C_3H_6O$ or $C_4H_8O$ group or a mixture of $C_2H_4O$, $C_3H_6O$ and $C_4H_8O$ groups, m is an integer of 1 to 100 and n is an integer of 1 to 100.

The use of ethoxylated castor oils for the deinking of printed wastepaper is known, for example, from JP 78/52705, reported in Chem. Abstr. 89, 131445j (1978), and from DE 21 48 590. The Japanese patent describes mixtures of castor oil with 10 to 400% ethylene oxide and ethoxylated nonylphenol which are suitable for the removal of printing inks from printed wastepaper. The process protected in DE-PS 21 48 590 is concerned with organic materials, for example paper, which are bleached with sodium chlorite in the presence of organic compounds containing at least one ethylene oxide and/or propylene oxide unit. Suitable organic compounds containing at least one alkylene oxide unit include inter alia ethoxylated castor oil.

Where ethoxylated castor oils are used, however, it has to be accepted that the quantities of castor oil and, hence, ethoxylated castor oils available on the market are subject to considerable fluctuations. Poor harvests in the main areas of cultivation, namely Brazil and India, result in shortages of the starting material, castor oil, at more or less long intervals. Accordingly, there is a need for a substitute for ethoxylated castor oils which, when used in processes for the regeneration of wastepaper, are at least comparable with the product to be replaced in regard to the deinking results obtained. Above all, the substitute product should be obtainable from a broader raw material base less vulnerable to crises and should be both ecologically and toxicologically safe.

It has now been found that certain carboxylic acid derivatives containing OH groups and/or carboxylic acids containing OH groups, which are alkoxylated with alkylene oxides, are eminently suitable as a replacement for ethoxylated castor oils in processes for the regeneration of wastepaper.

Accordingly, the present invention relates to a process for the regeneration of wastepaper which is characterized in that printed wastepaper is refined in known manner in the presence of alkoxylation products obtainable by reaction of alkylene oxides with $C_{10-22}$ carboxylic acid derivatives and/or $C_{10-22}$ carboxylic acids containing carboxylic acid residues with at least one OH group in the 9, 10, 13 and/or 14 position and the printing ink particles are subsequently removed from the fiber suspensions in known manner by flotation and/or washing.

The present invention also relates to the use of alkoxylation products obtainable by reaction of alkylene oxides with $C_{10-22}$ carboxylic acid derivatives and/or $C_{10-22}$ carboxylic acids containing carboxylic acid residues with at least one OH group in the 9, 10, 13 and/or 14 position for the regeneration of wastepaper.

The alkoxylation products to be used in accordance with the invention may be prepared by standard organic synthesis methods. Suitable starting materials for alkoxylated $C_{10-22}$ carboxylic acids containing OH groups are any unsaturated $C_{10-22}$ carboxylic acids of natural and/or synthetic origin which are free from OH groups and contain at least one or two double bonds in the 9- and/or 13-position, for example 9c-dodecenoic acid, 9c-tetradecenoic acid, 9c-hexadecenoic acid, 9c-octadecenoic acid, 9t-octadecenoic acid, 9c,12c-octadecadienoic acid, 9c, 12c,15c-octadecatrienoic acid, 9c-eicosenoic acid and/or 13c-docosenoic acid and/or mixtures having at least a high content of such unsaturated carboxylic acids. The educts used are preferably $C_{16-22}$ carboxylic acids containing at least one or two double bonds in the 9- and/or 13-position or carboxylic acid mixtures having at least a high content of $C_{16-22}$ carboxylic acids which contain at least one or two double bonds in the 9- and/or 13-position.

Suitable educts for alkoxylated $C_{10-22}$ carboxylic acid derivatives containing OH groups are any unsaturated, naturally occurring and/or synthetic $C_{10-22}$ carboxylic acid derivatives which are free from OH groups and contain carboxylic acid residues with at least one or two double bonds in the 9- and/or 13-position. Examples of unsaturated carboxylic acid residues containing 10 to 22 carbon atoms are the carboxylic acids already mentioned above. Unsaturated carboxylic acid derivatives containing $C_{16-22}$ carboxylic acid residues with at least one or two double bonds in the 9 and/or 13-position are preferred. Suitable unsaturated $C_{10-22}$ carboxylic acid derivatives are, for example, unsaturated $C_{10-22}$ carboxylic acid esters unsaturated $C_{10-22}$ carboxylic acid amides, unsaturated $C_{10-22}$ carboxylic acid mono- and/or di-$C_{1-4}$-alkylamides and/or unsaturated $C_{10-22}$ carboxylic acid mono- and/or di-$C_{1-4}$ alkanolamides. Unsaturated $C_{10-22}$ carboxylic acid alkyl esters containing 1 to 18 carbon atoms in the monohydric alcohol component and/or mono-, di- and/or triglycerides containing $C_{10-22}$ carboxylic acid residues with at least one or two double bonds in the 9- and/or 13-position are preferably used.

Examples of unsaturated $C_{10-22}$ carboxylic acid $C_{1-18}$ alkyl esters, which may be obtained in known manner by esterification of the corresponding unsaturated carboxylic acids or by transesterification of the corresponding mono-, di- and/or triglycerides with $C_{1-18}$ a alkyl alcohols, for example methanol, ethanol, propanal, butanol, isobutanol, 2-ethyl hexanol, decanol and/or stearyl alcohol, are palmitoleic acid methyl ester, oleic acid methyl ester, oleic acid ethyl ester, oleic acid isobutyl ester, oleic acid 2-ethyl hexyl ester and/or oleic acid decyl ester and/or $C_{10-22}$ carboxylic acids, $C_{1-18}$ a alkyl ester mixtures having at least a high content of such $C_{10-22}$ carboxylic acid $C_{1-18}$ a alkyl esters, which contain at least one or two double bonds in the 9-and/or 13-position in the carboxylic acid components, such as palm oil methyl ester, soybean oil methyl ester, rapeseed oil methyl ester and/or tallow fatty acid methyl ester. Suitable mono-, di- and/or triglycerides containing OH-free unsaturated $C_{10-22}$ carboxylic acid residues with at least one or two double bonds in the 9- and/or 13-position, are in particular fats and/or oils of natural origin of which the carboxylic acid content consists predominantly of unsaturated $C_{10-22}$ carboxylic acids with at least one or two double bonds in the 9- and/or 13-position, preferably predominantly of unsaturated $C_{16-22}$ carboxylic acids with at least one or two double bonds in the 9- and/or 13-position, such as olive oil, linseed oil, sunflower oil, safflower oil, soybean oil, peanut oil, cottonseed oil, rapeseed oil rich and/or poor in erucic acid, palm oil, lard and/or tallow.

The unsaturated $C_{10-22}$ carboxylic acid derivatives and/or unsaturated $C_{10-22}$ carboxylic acids are epoxidized by reaction with peracetic acid in the presence of acidic catalysts or with performic acid formed in situ from formic acid and hydrogen peroxide, for example by the process described in DE-PS 857 364. The epoxidation products obtained have iodine values below 20 and preferably below 15.

The oxirane rings of the epoxidized carboxylic acid derivatives and/or carboxylic acids are then opened by reaction with hydrogen or protic compounds, such as water, linear and/or branched $C_{1-18}$ alkyl and/or $C_{2-18}$ alkenyl alcohols or linear and/or branched, saturated and/or unsaturated $C_{1-22}$ carboxylic acids with formation of hydroxy groups. The ring opening conditions are selected so that the acid derivative groups and acid groups present remain intact.

The hydrogenation of epoxidized carboxylic acid derivatives and/or epoxidized carboxylic acids may be carried out, for example, by the process described in DE-OS 20 21 530 in the presence of catalysts based on heavy metals of the VIIIth group of the periodic system at temperatures in the range from 100° to 250° C. and under hydrogen pressures of $10^6$ to $5 \cdot 10^6$ Pa.

The reactions of epoxidized carboxylic acid derivatives and/or epoxidized carboxylic acids with protic compounds may be carried out by the processes described in M. S. Malinovskii "Epoxides and their Derivatives", Sivon Press, 1965, at temperatures in the range from 50° to 200 C. and under pressures of $10^5$ to $10^6$ Pa. The opening of the oxirane rings with linear and/or branched $C_{1-8}$ alkyl and/or $C_{1-6}$ alkenyl alcohols, preferably with linear and/or branched $C_{1-6}$ alkyl alcohols, is preferably carried out in the presence of acidic catalysts, such as sulfuric acid and/or p-toluene sulfonic acid.

The carboxylic acid derivatives and carboxylic acids obtainable by opening of the oxirane rings, which contain carboxylic acid residues bearing at least one OH group in the 9-, 10-, 13- and/or 14-position, are subsequently alkoxylated by known industrial methods, preferably with ethylene oxide, propylene oxide and/or butylene oxide and more preferably with ethylene oxide and/or propylene oxide, optionally in the presence of catalysts, for example potassium hydroxide and/or sodium methylate, at temperatures of 110° to 200° C. and preferably at temperatures of 140° to 175° C. and under pressures of $10^5$ to $2 \cdot 10^6$ Pa and preferably under pressures of $3 \cdot 10^5$ to $5 \cdot 10^5$ Pa (cf. for example "Chemische Technologie", Vol. 7, pages 131 to 132, Carl-Hanser-Verlag, München/Wein (1986)). The alkylene oxide content of the OH-containing carboxylic acid derivatives and/or carboxylic acids to be alkoxylated is from 2 to 400% and preferably from 40 to 200%, based on the non-alkoxylated compounds.

The alkoxylation products to be used in accordance with the invention, obtainable from $C_{10-22}$ carboxylic acid derivatives and/or $C_{10-22}$ carboxylic acids containing carboxylic acid residues with at least one OH group in the 9, 10, 13 and/or 14 position, are added to paper stock suspensions in quantities of preferably 0.02 to 2% by weight and, more preferably, 0.1 to 0.8% by weight, based on air dry paper stock. Air-dry paper stock means that an equilibrium state of internal moisture has established itself in the paper stock. This equilibrium state depends both on the temperature and on the relative humidity of the air.

In many cases, the deinking result, i.e. the removal of printing inks from printed wastepaper, can be improved by using the alkoxylation products to be used in accordance with the invention in combination with, for example, $C_{10-22}$ fatty acids, such as Olinor®4010, Olinor®4020 and/or Olinor®DG40 (all products of Henkel KGaA), ethoxylated $C_{6-22}$ alcohols, ethoxylated alkylphenols, polymers, such as polyacrylamides and/or polydimethylaminoethyl methacrylic acid, and/or copolymers of the type described, for example, in DE 38 39 479. The total quantity of these optional constituents is between 0.1 and 1% by weight, based on air-dry paper stock.

In the presence of alkoxylation products according to the invention, water-dilutable and/or solvent-containing printing inks, preferably water-dilutable printing inks, for example rotary newsprint inks, book printing inks, offset printing inks, illustration intaglio printing inks, flexographic printing inks, laser printing inks and/or packaging intaglio printing inks, may be removed from printed wastepaper, for example newspapers, magazines, computer paper, journals, brochures, forms, telephone directories and/or catalogues. The deinked wastepaper obtained is distinguished by very high degrees of whiteness.

Printed wastepaper is refined in a pulper at 20 to 60° C. at a pulp density of, for example, 1 to 5% by weight in an aqueous solution typically containing 0.1 to 1.5% by weight 100% hydrogen peroxide, 0 to 2.5% by weight 99% by weight NaOH, 0 to 4.0% by weight soda waterglass, solids content 35% by weight (37 to 40 Be), 0.02 to 2% by weight alkoxylated OH-containing carboxylic acid derivatives and/or carboxylic acids according to the invention and 0 to 1% by weight of the optional constituents mentioned above (all percentages by weight based on air-dry wastepaper). After a residence time of 60 to 120 minutes at temperatures in the range from 20° to 60° C., the paper stock suspensions are stirred into water or water is added to them so that 0.6 to 1.6% by weight stock suspensions are obtained. The detached printing ink particles are then removed from the stock suspensions in known manner by washing out or by flotation (Ullmanns Enzyklopädie der technischen Chemie, 4th Edition, Vol. 17, pages 570 to 571 (1979)). Flotation is preferably carried out in known manner, for example in a Denver flotation cell.

EXAMPLES

1. Preparation of ethoxylated soybean oil containing OH groups from hydrogenated soybean oil epoxide (soybean oil—EO I)

20 kg epoxidized soybean oil (approximate fatty acid composition: 8% by weight palmitic acid, 4% by weight stearic acid, 28% by weight oleic acid, 53% by weight linoleic acid and 6% by weight linolenic acid; epoxide content = 6.78% by weight; iodine value = 5; acid value = 0.4) and 0.2 kg of a nickel catalyst (support: kieselguhr) were introduced into an autoclave, the air present in the reactor was displaced by purging with nitrogen and the contents of the reactor were hydrogenated at 150° to 170° C. under a hydrogen pressure of $2 \cdot 10^6$ Pa until no more hydrogen was taken up (approx. 6 hours). After cooling and separation of the catalyst, 20 kg colorless hydrogenated soybean oil epoxide having an OH value (OHV) of 165.8, a saponification Value (SV) of 181.4, an iodine value (IV) of 8.3 and an acid value (AV) of 1 were obtained.

5.0 g of a 30% by weight solution of potassium hydroxide in methanol were added to 650 g of the hydrogenated soybean oil epoxide, followed by heating in an autoclave to 100° C. The traces of methanol present were removed at that temperature by evacuation and purging with nitrogen five times. After the reaction temperature had been increased to 150° C., a total of 308 g ethylene oxide was added in portions so that the pressure in the reactor did not exceed a value of $5 \cdot 10^5$ Pa. On completion of the reaction, the reaction mixture was cooled to around 90° C. and the autoclave evacuated for about 15 minutes to remove any traces of ethylene oxide still present. A clear yellow liquid having an OHV of 124.5 was obtained.

Preparation of ethoxylated and propoxylated soybean oil containing OH groups from hydrogenated soybean oil epoxide (soybean oil—EO/PO I)

6.2 g of a 30% by weight solution of potassium hydroxide in methanol were added to 371 g of the soybean oil epoxide hydrogenated in accordance with Example 1 and the resulting mixture was reacted first with 440 g ethylene oxide and then, in the same reactor, with 232 g propylene oxide under the same conditions as in Example 1. After removal of traces of propylene oxide in vacuo and neutralization of the catalyst with 3.3 g lactic acid, a golden yellow liquid having an OHV of 72.1 was obtained.

3. Preparation of ethoxylated linseed oil containing OH groups from hydrogenated linseed oil epoxide (linseed oil—EO I)

As in Example 1, 200 g epoxidized linseed oil (approximate fatty acid composition: 5% by weight palmitic acid, 4% by weight stearic acid, 22% by weight oleic acid, 17% by weight linoleic acid and 52% by weight linolenic acid; epoxide content: 8.9% by weight; iodine value 10; acid value 0.7) and 15 g of a nickel catalyst (support: kieselguhr) were initially introduced into an autoclave, the air present in the reactor was displaced by purging with nitrogen and the contents of the reactor were hydrogenated at 150° to 170° C. under a hydrogen pressure of $2 \cdot 10^6$ Pa until no more hydrogen was taken up. After cooling and separation of the catalyst, colorless hydrogenated linseed oil epoxide having an OHV of 202.6, an SV of 178.2, an IV of 16.9 and an AV of 0.7 was obtained.

650 g of the hydrogenated linseed oil epoxide were reacted with 30S g ethylene oxide as in Example 1. A yellow liquid having an OHV of 152 was obtained.

4. Preparation of ethoxylated soybean oil containing OH groups from soybean oil epoxide reacted with methanol (soybean oil—EO II)

2360 (10 mol) epoxidized soybean oil (characteristics as in Example 1) were added dropwise with intensive cooling to a refluxed solution of 9 g (0.9 g/mol epoxide) concentrated sulfuric acid in 960 g (30 mol) methanol. After the epoxide had been added and reacted off, the reaction mixture was neutralized with diethyl ethanolamine and excess methanol was removed in vacuo. A clear yellow liquid having an OHV of 165, an SV of 163, an IV of 19.4 and an AV of 1.6 was obtained.

7.5 g of a 30% by weight methanolic sodium methylate solution were added to 510 g of the ring opening product of soybean oil epoxide with methanol and the resulting mixture reacted with 551 g ethylene oxide at 175° C. under the same conditions as in Example 1. After traces of ethylene oxide had been removed in vacuo, a red-brown liquid having an OHV of 110.6 was obtained.

5. Preparation of ethoxylated and propoxylated soybean oil containing OH groups from soybean oil epoxide reacted with methanol (soybean oil—EO/PO II)

7.5 g of a 30% by weight methanolic sodium methylate solution were added to 510 g of the ring opening product of soybean oil epoxide with methanol of Example 4 and the resulting mixture reacted first with 551 g ethylene oxide under the same conditions as in Examples 1 and 2. After traces of propylene oxide had been removed in vacuo, a brown-yellow, almost clear liquid having an OHV of 94.9 was obtained.

6. Preparation of ethoxylated soybean oil containing OH groups from soybean oil epoxide reacted with carboxylic acids (soybean oil epoxide—EO III)

126 kg (805 mol) of a mixture of saturated fatty acids (60% by weight octanoic acid, 35% by weight decanoic acid, 3% by weight dodecanoic acid and 2% by weight hexanoic acid; AV = 361.9, IV < 1) and 180 kg (766 mol) epoxidized soybean oil (characteristics as in Example 1) were introduced into a stirred tank and heated with stirring to 170° C. When the reaction mixture contained no more epoxide groups (approx. 4 hours), it was distilled in vacuo up to about 190° C. A dark yellow liquid having an OHV of 84.6, an SV of 239 and an AV of 2.4 was obtained.

6.9 g of a 30% by weight solution of potassium hydroxide in methanol were added to 423 g of the reaction product soybean oil epoxide with carboxylic acids and the remixture reacted with 660 g ethylene oxide at 140° C. as in Example 1. After traces of ethylene oxide had been removed in vacuo, followed by neutralization with lactic acid, a dark yellow liquid having an OHV of 54.7 was obtained.

100 g air-dry (=90 g bone-dry at 10% humidity) printed wastepaper of 50% by weight magazines and 50% by weight newspapers were refined with an aqueous solution containing 2 g soda waterglass, 37 to 40·Be (35% by weight),
1 g sodium hydroxide (99% by weight),
0.7 g hydrogen peroxide (100% by weight),
0 15 or 0.4 g alkoxylated compounds containing OH groups according to the invention in a laboratory pulper (pulp density 3% by weight) for 15 minutes at 45° C. using a dispersion disk rotating at 3,500 revolutions per minute and, after 105 minutes at 45° C., were diluted to 1% by weight by stirring the stock suspensions into water. The stock suspensions were then floated for 12 minutes at 45° C. in a Denver flotation cell at 1,000 revolutions per minute.

The deinking results are shown in Table 1. The deinkability value (DIV) was calculated from the reflection factors $R_{457nm}$ (whiteness) of the printed (BS), deinked (DS) and unprinted (US) paper stocks in accordance with the following formula:

$$DIV(\%) = \frac{\text{whiteness }(DS) - \text{whiteness }(BS)}{\text{whiteness }(US) - \text{whiteness }(BS)} \times 100$$

(0 % signifies no removal of printing ink, 100% signifies quantitative removal of printing ink).

TABLE 1

| Alkoxylation product used | Quantity of alkoxylation product used in g per 100 g air-dry printed wastepaper | $R_{457}$ (BS) | $R_{457}$ (DS) | $R_{457}$ (US) | DIV (%) |
|---|---|---|---|---|---|
| Soybean oil - EO I | 0.4 | 39.7 | 56.2 | 61.4 | 76.0 |
| Linseed oil - EO I | 0.4 | 35.2 | 54.1 | 60.2 | 75.6 |
| Soybean oil - EO/PO I | 0.15 | 40.2 | 57.1 | 61.7 | 78.6 |
| Soybean oil - EO II | 0.15 | 40.2 | 56.4 | 61.7 | 75.3 |
| Soybean oil - EO/PO II | 0.15 | 40.2 | 57.1 | 61.7 | 78.6 |
| Soybean oil - EO III | 0.15 | 40.2 | 57.6 | 61.7 | 80.9 |

We claim:

1. A process for the regeneration of printing ink containing wastepaper comprising the steps of:
   A. fiberizing the wastepaper in an aqueous alkaline deinking solution containing a deinking effective quantity of at least one alkoxylation product of an alkylene oxide and a $C_{10-22}$ carboxylic acid or derivative thereof containing an OH group in one or more of the 9, 10, 13 and 14 positions on the carboxylic acid or derivative thereof, to detach ink particles from the wastepaper; and
   B. removing the detached ink particles from the deinking solution.

2. The process of claim 1 wherein the at least one alkoxylation product is present in the deinking solution in from about 0.02 to about 2% by weight, based on the weight of the air dry wastepaper therein.

3. The process of claim 2 wherein the at least one alkoxylation product is present in from about 0.1 to about 0.8% by weight.

4. The process of claim 1 wherein the deinking solution also contains at least one of the following:
   a) an alkali metal hydroxide,
   b) an alkali metal silicate,
   c) a soap,
   d) an ethoxylated fatty alcohol,
   e) an ethoxylated alkyl phenol,
   f) an oxidative bleach,
   g) a $C_{10-22}$ fatty acid, and
   h) a polymer.

5. The process of claim 1 wherein the deinking solution also contains
   a) from about 0.1 to about 1.5% by weight of hydrogen peroxide,
   b) from 0 to about 2.5% by weight of sodium hydroxide,
   c) from 0 to about 4.0% by weight of sodium silicate, and
   d) from 0 to a total of about 1% by weight of one or more of a $C_{10-22}$ fatty acid, an ethoxylated $C_{6-22}$ alcohol, and a polymer, wherein the above weights are based on the air dry weight of the wastepaper.

6. The process of claim 1 wherein the at least one alkoxylation product is one or more of the following derivatives of a $C_{10-22}$ carboxylic acid or mixture of such acids:
   a) an ester thereof with a $C_{1-18}$ monohydric alcohol,
   b) a mono-, di-, or tri-glyceride thereof,
   c) an amide thereof,
   d) a mono- or di- $C_{1-4}$ alkylamide thereof, and
   e) a mono- or di- $C_{1-4}$ alkanolamide thereof.

7. The process of claim 1 wherein step A is carried out at a temperature of about 20° to about 60° C.

8. The process of claim 1 wherein from about 1 to about 5% by weight, based on the weight of the aqueous solution, of wastepaper is present in the deinking solution.

9. The process of claim 1 wherein the at least one alkoxylation product contains from about 2 to about 400% by weight of alkylene oxide based on the nonalkoxylated carboxylic acid or derivative thereof.

10. The process of claim 9 wherein from about 40 to about 200% by weight of alkylene oxide is present in the at least one alkoxylation product based on the nonalkoxylated carboxylic acid or derivative thereof.

11. The process of claim 1 wherein the alkylene oxide component of the at least one alkoxylation product is one or more of ethylene oxide, propylene oxide, and butylene oxide.

12. The process of claim 1 wherein the at least one alkoxylation product contains a $C_{16-22}$ carboxylic acid moiety.

13. The process of claim 1 wherein the at least one alkoxylation product contains a $C_{16-22}$ carboxylic acid moiety, the alkylene oxide component thereof is one or both of ethylene oxide and propylene oxide, and from about 40 to about 200% by weight of the alkylene oxide is present therein.

* * * * *